United States Patent [19]
Chen

[11] Patent Number: 5,860,949
[45] Date of Patent: *Jan. 19, 1999

[54] VOLUME HOMEOSTATIC FLUID-FLUID EXCHANGER

[76] Inventor: Jen-Yie Chen, 15F-3 No.417, Tashun 2 Rd. Sanmin District, Kaohsiung, Taiwan

[ * ] Notice: The term of this patent shall not extend beyond the expiration date of Pat. No. 5,755,684.

[21] Appl. No.: 968,061

[22] Filed: Nov. 12, 1997

Related U.S. Application Data

[63] Continuation of Ser. No. 770,297, Dec. 20, 1996, Pat. No. 5,755,684.

[51] Int. Cl.$^6$ ........................................... A61M 1/00
[52] U.S. Cl. .................................................. 604/35
[58] Field of Search ............................... 604/4–9, 27, 28, 604/30–32, 35–38, 118, 121, 181–185, 187, 246, 248

[56] References Cited

U.S. PATENT DOCUMENTS

| | | |
|---|---|---|
| 4,191,176 | 3/1980 | Spina et al. . |
| 4,340,037 | 7/1982 | Lewicky . |
| 5,304,118 | 4/1994 | Trese et al. . |
| 5,328,481 | 7/1994 | Wang . |
| 5,364,374 | 11/1994 | Morrison et al. . |
| 5,411,490 | 5/1995 | Tennican et al. . |
| 5,454,792 | 10/1995 | Tennican et al. . |
| 5,755,684 | 5/1998 | Chen ......................................... 604/35 |

*Primary Examiner*—John D. Yasko
*Assistant Examiner*—Manuel Mendez
*Attorney, Agent, or Firm*—Bacon & Thomas, PLLC

[57] ABSTRACT

A volume homeostatic fluid—fluid exchanger for facilitating clearance of postvintrectomy vitreous hemorrhage includes an infusion cylinder device, an aspiration cylinder device, and a connecting tube which interconnects one cylinder of each of the two cylinder devices to form a close hydraulic system and establish a synchronized action between the two cylinder devices. When a first plunger device of one of the two cylinder devices acts, a second plunger device of the other cylinder device simultaneously moves to an opposite direction of equal displacement due to a synchronized hydraulic action. When one pushes the plunger device of the infusion cylinder device, a liquid medicine is infused into the vitreous cavity via a first needle, and equal amount of bloody fluid is aspirated from the vitreous cavity by the aspiration cylinder device via a second needle. After changing flow directions inside the cylinder devices, one can refill the infusion cylinder device with the liquid medicine and in the same time drain the bloody fluid out of the aspiration cylinder device. Repeat the steps mentioned above, the content of the vitreous cavity can be replaced by the liquid medicine under constant intra-ocular pressure (IOP).

8 Claims, 5 Drawing Sheets

VOLUME HOMEOSTATIC FLUID-FLUID EXCHANGER

This application is a Continuation of application Ser. No. 08/770,297, filed Dec. 20, 1996, now U.S. Pat. No. 5,755,684.

BACKGROUND OF THE INVENTION

1. Field of the Invention

The present invention relates to a volume homeostatic fluid—fluid exchanger which can facilitate the clearance of post-vitrectomy vitreous hemorrhage. The present invention also relates to a new method for managing the recurrent vitreous hemorrhage in proliferative diabetic retinopathy after posterior vitrectomy.

2. Description of the Related Art

A number of methods for performing a vitrectomy have heretofore been disclosed, an example of which is disclosed U.S. Pat. No. 5,304,118 to Trese et al, incorporated herein for reference. The management of proliferative diabetic retinopathy (PDR) is very difficult. Despite the successful posterior vitrectomy with complete membrane peeling, the incidence of post-operation recurrent hemorrhage is relatively high, up to 29% to 75% (Mieler W F, Wolf M D. In: Lewis H, Ryan S J, editors. Medical and Surgical Retina. St. Louis; Mosby, 1994; 330–340). In previous experience, in addition to observation for two or three months to see whether the recurrent hemorrhage can be absorbed per se, there are two surgical methods to manage the recurrent hemorrhage, including: fluid-gas exchange method and vitreous cavity lavage method. In the fluid-gas exchange method, air is used to replace the bloody fluid in the eyeball, yet the intra-ocular pressure (IOP) cannot be maintained constant during the procedure such that the oozing rate is rather high. In addition, when air bubble presents in the vitreous cavity, the patient sees nothing; when the air bubble disappears, the recurrent hemorrhage often results again from the oozing due to fluctuation of the intra-ocular pressure. Thus, the fluid-gas exchange cannot offer useful vision immediately after the procedure.

The conventional vitreous cavity lavage method, although having the potential to improve vision immediately after the procedure, still has two drawbacks: unstable IOP and the necessity of the larger caliber needle. The drainage needle, although of larger caliber, cannot aspirate the bloody fluid actively. In addition, although the caliber of the drainage needle could be rather large, the drainage needle still tends to be blocked by a blood clot or residual vitreous fiber. The procedure of vitreous lavage will thus be interrupted. Meanwhile, larger drainage needles induce larger wounds, more trauma, and higher incidence of recurrent hemorrhage.

The present invention is intended to provide an apparatus which mitigates and/or obviates the above problems.

SUMMARY OF THE INVENTION

It is an object of the present invention to provide a volume homeostatic fluid—fluid exchanger which may maintain the intra-ocular pressure constant during the vitreous cavity lavage, such that the rate of post-operation oozing decreases, and the patient feels no subjective discomfort during operation and could regain useful vision immediately after procedure.

It is a further object of the present invention to provide an active volume homeostatic fluid—fluid exchange which uses small needles to reduce trauma to a minimized manner, while the procedure can be performed under local anesthesia and the incidence of post-operation wound leakage can be deceased which also lessens the possibility of recurrent hemorrhage.

The above objects are achieved by providing a volume homeostatic fluid—fluid exchanger which comprises an infusion cylinder means, an aspiration means, first and second control means, and first and second needle means.

The infusion cylinder means includes a first chamber and a second chamber defined therein. Each of the first chamber and the second chamber has a first plunger slidably received therein, the first plungers being connected to move simultaneously. The aspiration cylinder means includes a third chamber and a fourth chamber defined therein. Each of the third chamber and the fourth chamber has a second plunger slidably received therein, the second plungers being connected to move simultaneously. The first chamber and the fourth chamber are identical in the diameters thereof, and the second chamber and the third chamber are identical in the diameters thereof.

The first control valve includes a first port, a second port in fluid communication with a liquid medicine source, and a third port in fluid communication with the first chamber of the infusion cylinder means. When the first control valve is in a first status, the first port is in fluid communication with the third port. When the first control valve is in a second status, the second port is in fluid communication with the third port.

The second control valve includes a first port, a second port in fluid communication with a drainage tube, and a third port in fluid communication with the fourth chamber of the aspiration cylinder means. When the second control valve is in a first status, the first port of the second control valve is in fluid communication with the third port of the second control valve. When the second control valve is in a second status, the second port of the second control valve is in fluid communication with the third port of the second control valve.

The first needle means includes a first end and a second end. A first needle is attached to the first end of the first needle means, while the second end of the first needle means is in fluid communication with the first port of the first control valve. The second needle means includes a first end and a second end. A second needle is attached to the first end of the second needle means, while the second end of the second needle means is in fluid communication with the first port of the second control valve.

In addition, a connecting tube is interconnected between the second chamber of the infusion cylinder means and the third chamber of the aspiration cylinder means. A fluid is contained in the second chamber, the third chamber, and the connecting tube.

By such an arrangement, when the plungers of one of the infusion cylinder means and the aspiration cylinder means move in a direction, the plungers of the other of the infusion cylinder means and the aspiration cylinder means synchronously move to an opposite direction of equal displacement.

Other objects, advantages, and novel features of the invention will become more apparent from the following detailed description when taken in conjunction with the accompanying drawings.

DESCRIPTION OF THE PREFERRED EMBODIMENT

Figure 1:
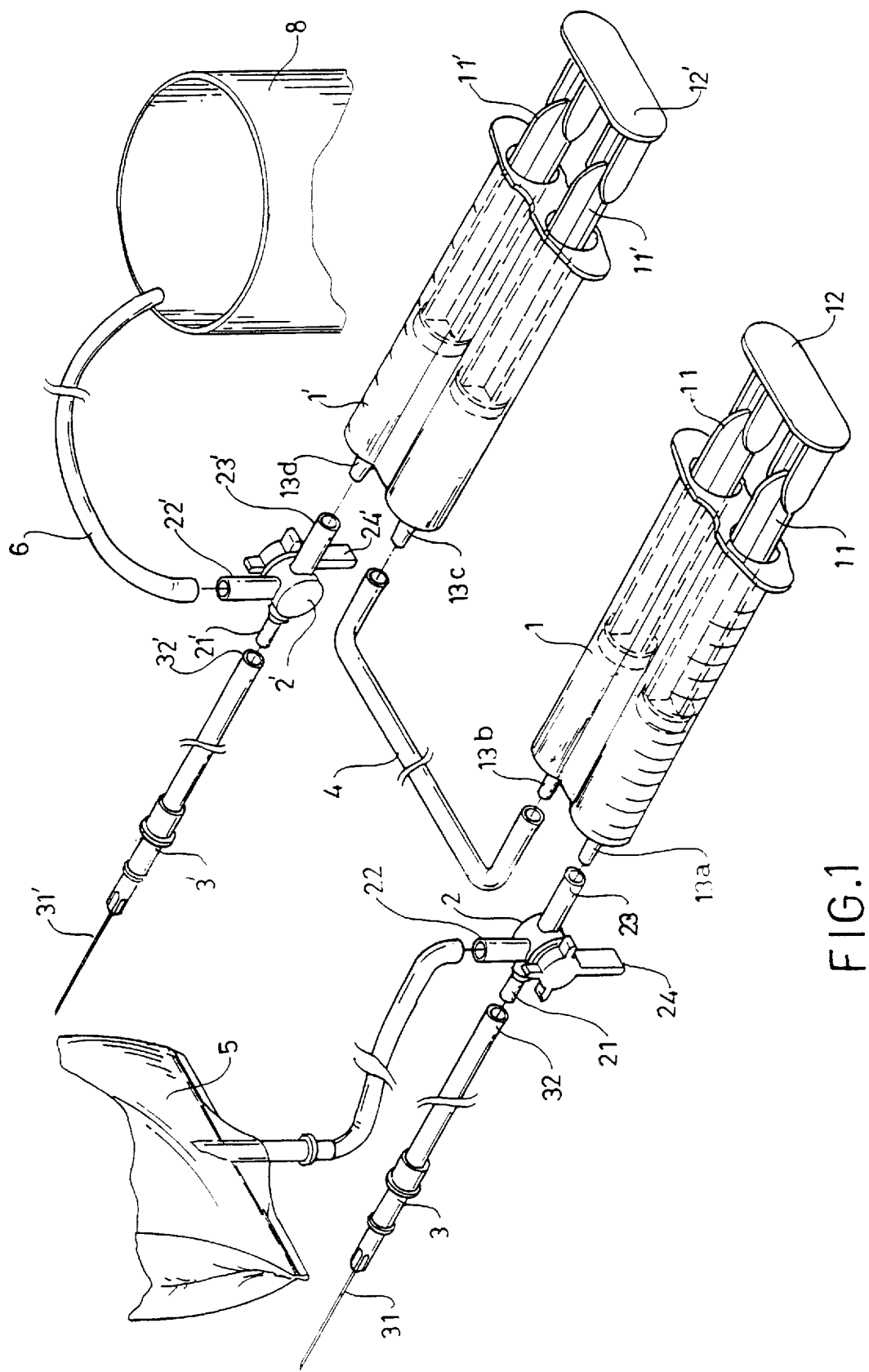
FIG. 1 is a perspective view, partly exploded, of a volume homeostatic fluid—fluid exchanger in accordance with the present invention.
Figure 2:
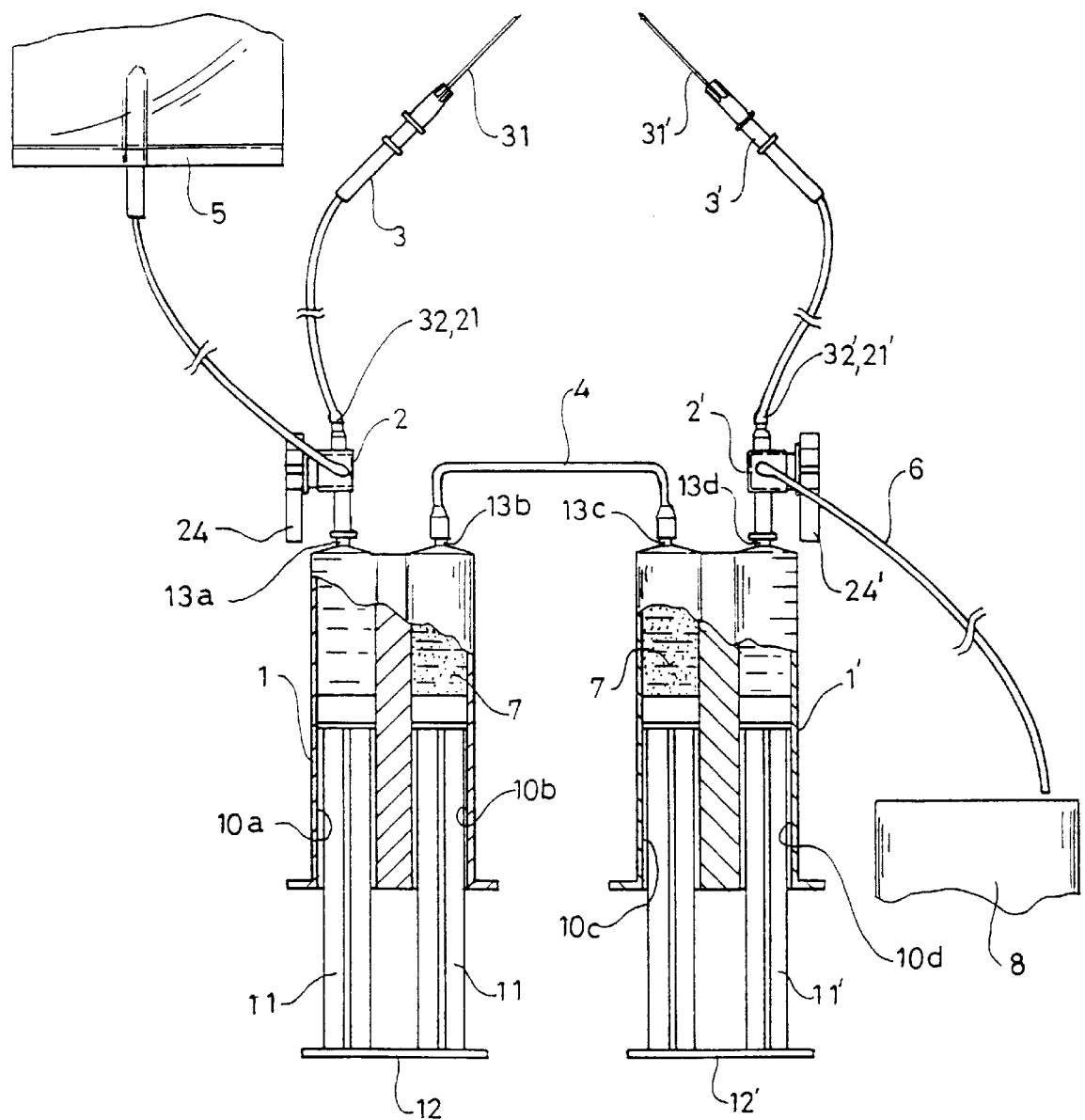
FIG. 2 is an elevational view, partly sectioned, of the volume homeostatic fluid—fluid exchanger in accordance with the present invention.

Referring to the drawings and initially to FIGS. 1 and 2, a volume homeostatic fluid—fluid exchanger in accordance with the present invention generally includes an infusion cylinder means 1, an aspiration cylinder means 1', first and second control valves 2 and 2', first and second needle means 3 and 3' and a connecting tube 4. The infusion cylinder means 1 includes a first chamber 10a and a second chamber 10b defined therein. Each of the first chamber 10a and the second chamber 10b has a first plunger 11 slidably received therein. The two first plungers 11 are connected via a first plate 12 so as to move simultaneously. The infusion cylinder means 1 further comprises a first nozzle 13a and a second nozzle 13b which are respectively in fluid communication with the first chamber 10a and the second chamber 10b. As shown in FIG. 2, the aspiration cylinder means 1' includes a third chamber 10c and a fourth chamber 10d defined therein. Each of the third chamber 10c and the fourth chamber 10d has a second plunger 11' slidably received therein. The two second plungers 11' are connected via a second plate 12' so as to move simultaneously. The aspiration cylinder means 1' further comprises a third nozzle 13c and a fourth nozzle 13d which are respectively in fluid communication with the third chamber 10c and the fourth chamber 10d. The first chamber 10a and the fourth chamber 10d are identical in the diameters thereof. The second chamber 10b and the third chamber 10c are identical in the diameters thereof.

Figure 5:
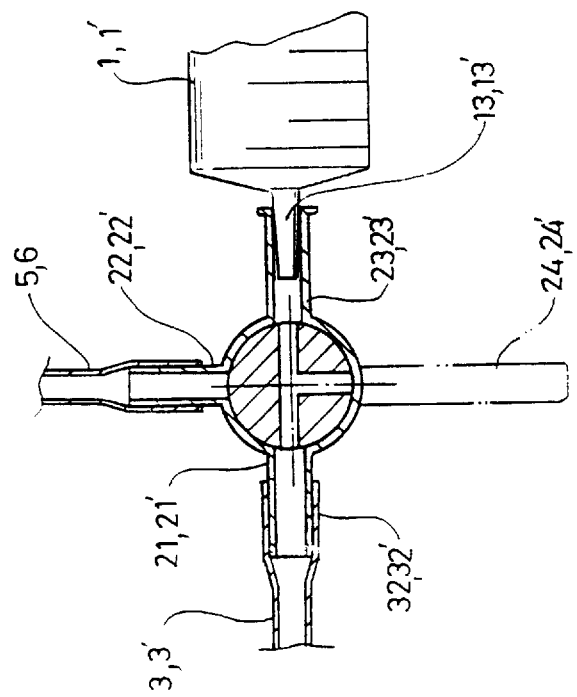
FIG. 5 is a cross sectional view taken along line V—V in FIG. 3, illustrating a control valve of the volume homeostatic fluid—fluid exchanger.

Referring to FIGS. 1, 2, and 5, the first control valve 2 is substantially a three-way valve and includes a first port 21 in fluid communication with the first needle means 3, a second port 22 in fluid communication with a liquid medicine source 5, and a third port 23 in fluid communication with the first chamber 10a via the first nozzle 13a. The liquid medicine source 5 is, e.g, a normal saline, a latic ringer, or any other suitable isotonic salt solution. The first control valve 2 further includes a first control handle 24, wherein when the first control handle 24 is in a first position, the first port 21 is in fluid communication with the third port 23 (see FIG. 5), and when the first control handle 24 is in a second position, the second port 22 is in fluid communication with the third port 23 (see FIG. 6).

Still referring to FIGS. 1, 2, and 5, the second control valve 2' is also a three-way valve and includes a first port 21' in fluid communication with the second needle means 3', a second port 22' in fluid communication with a drainage tube 6 (which, in turn, is in fluid communication with a drainage bag or drainage container 8, see FIGS. 1 to 4), and a third port 23' in fluid communication with the fourth chamber 10d via the fourth nozzle 13d. Similarly, the second control valve 2' further includes a second control handle 24', wherein when the second control handle 24' is in a first position, the first port 21' is in fluid communication with the third port 23' (see FIG. 5), and when the second control handle 24' is in a second position, the second port 22' is in fluid communication with the third port 23' (see FIG. 6).

A first needle 31 (of small caliber) is attached to a first end of the first needle means 3, while a second end of the first needle means 3 is in fluid communication with the first port 21 of the first control valve 2 via a connecting tube 32. Similarly, a second needle 31' (of small caliber) is attached to a first end of the second needle means 3', while a second end of the second needle means 3' is in fluid communication with the first port 21' of the second control valve 2' via another connecting tube 32'.

The connecting tube 4 is interconnected between the second nozzle 13b and the third nozzle 13c, thereby providing a fluid communication therebetween. A fluid 7 is contained in the connecting tube 4, the second chamber 10b, and the third chamber 10c.

By such an arrangement, when the plungers of one of the two cylinder means act, the plungers of the other cylinder means simultaneously move to an opposite direction of equal displacement due to a synchronized hydraulic action.

Figure 3:
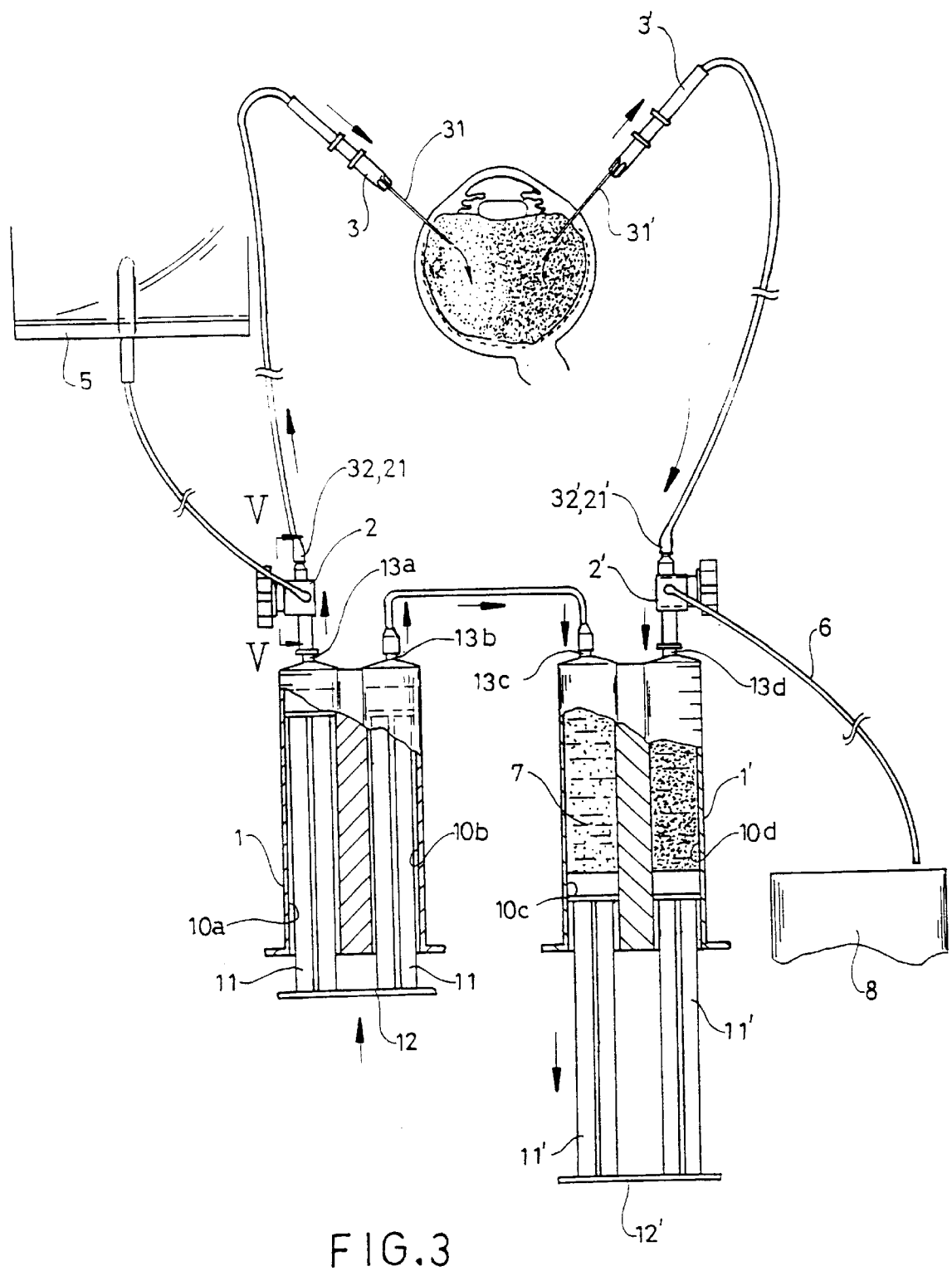
FIGS. 3 and 4 are elevational views, partly sectioned, illustrating operation of the volume homeostatic fluid—fluid exchanger in accordance with the present invention.
Figure 4:
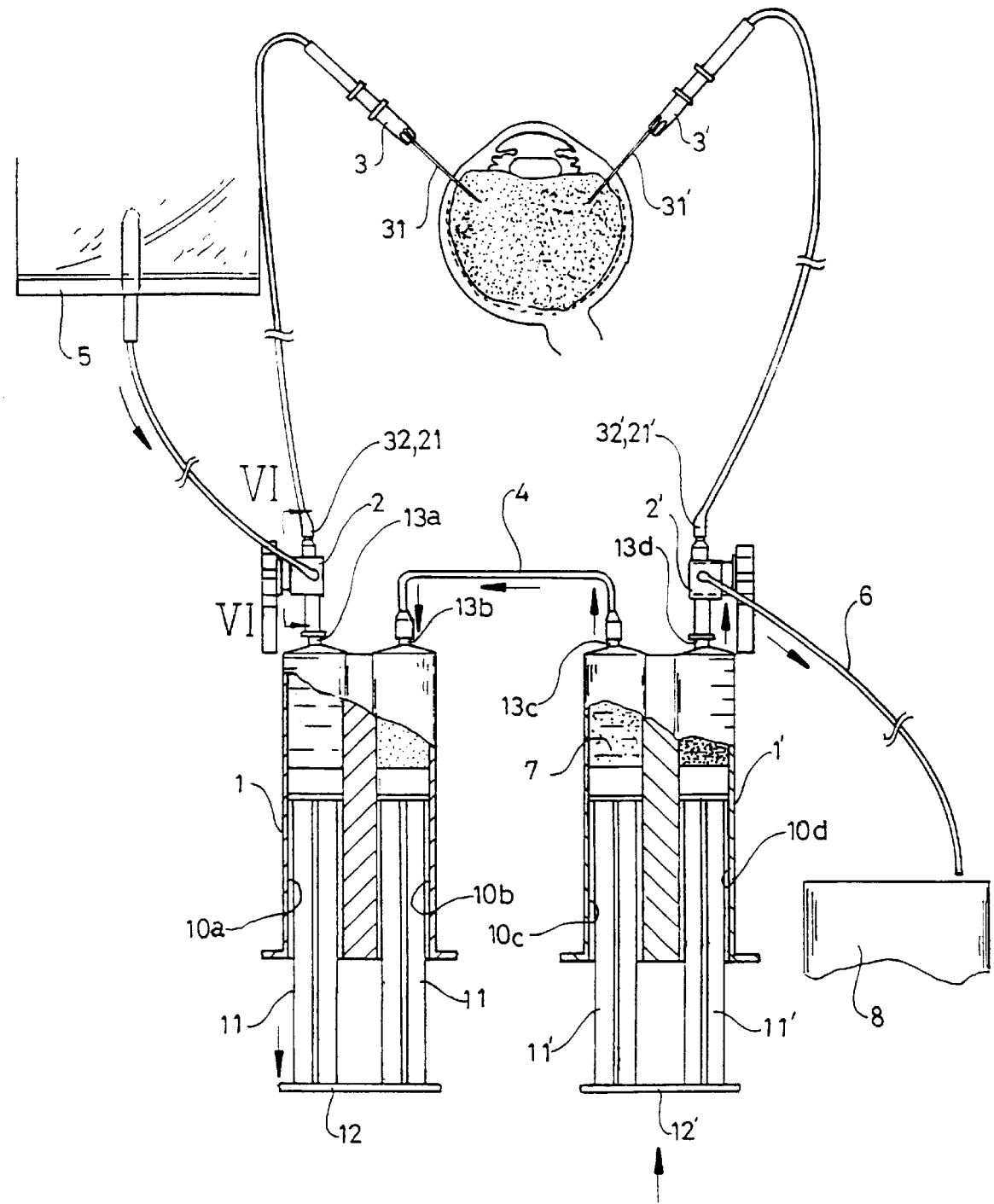

Referring to FIG. 3, when in use, the first needle 31 and the second needle 31' respectively pierce into a vitreous cavity (not labeled) via pars plana (not labeled), and the control handles 24 and 24' are both switched to the first positions wherein the first port 21, 21' is in fluid communication with the third port 23, 23' while the second port 22, 22' is in a closed status, as shown in FIG. 5. Then, the first plate 12 together with the first plungers 11 are pushed toward the first and second nozzles 13a and 13b, such that the liquid medicine inside the first chamber 10a of the first cylinder means 1 is infused into the vitreous cavity via the third port 23 and the first port 21 of the first control valve 2 and the first needle means 3. In the mean time, the fluid 7 inside the second chamber 10b of the infusion cylinder means 1 flows into the third chamber 10c of the aspiration cylinder means 1' to synchronously move the second plate 12' together with the second plungers 11' away from the third and fourth nozzles 13c and 13d, such that bloody fluid is removed from the vitreous cavity and passed through the second needle means 3', the first port 21' and the third port 23' of the second control valve 2', and finally enters the fourth chamber 10d of the second cylinder means 1'. In other words, since the first chamber 10a and the fourth chamber 10d are identical in the diameters thereof and the second chamber 10b and the third chamber 10c are identical in the diameters thereof, a quantity of the liquid medicine identical to that of the bloody fluid removed is infused into the vitreous cavity, thereby maintaining the intra-ocular pressure (IOP) constant. Generally, small and unorganized blood clot can be removed from this active aspiration mechanism, yet if the second needle 31' is blocked by a larger or organized blood clot, one can temporarily reverse the infusion/aspiration procedure by moving the second plungers 11' in an opposite direction so as to expel the clot from the aspiration needle (i.e., the second needle 31') and then restart the fluid—fluid exchange while maintaining the IOP constant.

Figure 6:
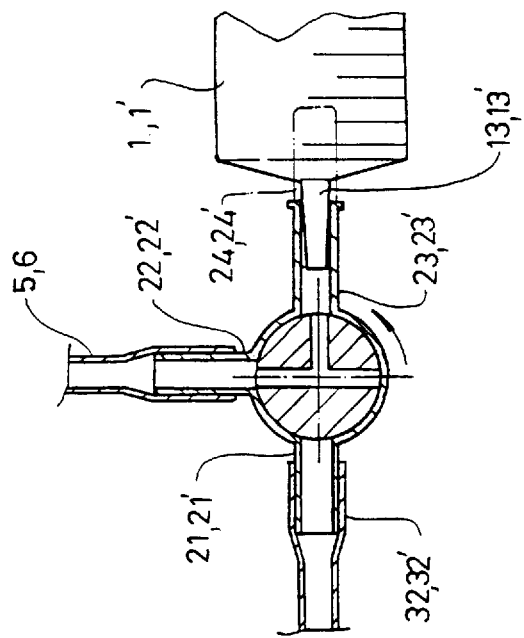
FIG. 6 is a cross sectional view taken along line VI—VI in FIG. 4, illustrating another status of the control valve.

Thereafter, the control handles 24 and 24' are switched to the second positions shown in FIG. 6 such that the second port 22, 22' is in fluid communication with the third port 23, 23'. Then, the second plate 12' together with the second plungers 11' are moved toward the third and fourth nozzles 13c and 13d, such that the bloody fluid inside the fourth chamber 10d of the aspiration cylinder means 1' is drained via the drainage tube 6., while the liquid medicine from the liquid medicine source enters the first chamber 10a of the infusion cylinder means 1 for subsequent synchronized infusion/aspiration. Repeat the above steps, the content of the vitreous cavity can be replaced with liquid medicine under constant IOP.

It is appreciated that the bloody fluid concentration will dramatically be reduced to 0.03% after proceeding with replacement of the bloody fluid with the liquid medicine by a volume (about 40 c.c.) approximately eight times of that of the vitreous cavity. It is further appreciated that the connecting tube 4 may be of rigid material or other suitable material which does not deform under the fluid pressure so as to maintain the synchronized hydraulic motion.

According to the above description, it is appreciated that the volume homeostatic fluid—fluid exchanger of the present invention has the following advantages:

(1) Constant IOP: Due to simultaneous infusion of the liquid medicine and aspiration of the bloody fluid of equal amount into and from the vitreous cavity, the IOP can be maintained constant through procedure. Because the infusion and aspiration mechanisms are synchronized, the IOP is not influenced by the speed of fluid exchange, and the patient feels no subjective discomfort during operation and could regain useful vision immediately after procedure.

(2) Small wound: Because both the infusion and aspiration mechanisms are active, the caliber of infusion and aspiration needles can be very small and thus result in minimized trauma. This procedure can be performed under local anesthesia and the incidence of post-operation wound leakage can be deceased, thus also lessens the possibility of recurrent hemorrhage.

(3) Less subjective to the influence of blood clot: Small and unorganized blood clot can be removed from the active aspiration mechanism. If the aspiration needle is blocked by a larger or organized blood clot, one can temporarily reverse the infusion/aspiration procedure to expel the clot from the aspiration needle and then restart the fluid—fluid exchange while maintaining a constant IOP.

(4) Increased intra-operative and post-operative clearance rate of vitreous cavity lavage: The volume homeostatic fluid—fluid exchanger of the present invention, as having the above three advantages, may increase both the intra-operative and post-operative clearance rate of vitreous cavity lavage.

Although the invention has been explained in relation to its preferred embodiment, it is to be understood that many other possible modifications and variations can be made without departing from the spirit and scope of the invention as hereinafter claimed.

What is claimed is:

1. A volume homeostatic fluid—fluid exchanger comprising:
an infusion means including a first chamber and a second chamber defined therein, each of the first chamber and the second chamber having a first plunger slidably received therein, the first plungers being connected to move simultaneously;
an aspiration means including a third chamber and a fourth chamber, each of the third and the fourth chamber having a second plunger slidably received therein, the second plungers being connected to move simultaneously;
a connecting tube interconnected between the second chamber of the infusion means and the third chamber of the aspiration means, and a fluid being contained in the second chamber, the third chamber and the connecting tube;
whereby the first plunger of the first chamber of the infusion means moves in a direction, the second plunger of the fourth chamber of the aspiration means synchronously moves to a reverse direction of equal displacement due to the hydrodynamic synchronized action between the second chamber of the infusion means and the third chamber of the aspiration means.

2. The volume homeostatic fluid—fluid exchanger according to claim 1, further comprising a first needle device in fluid communication with the first chamber of the infusion means and a second needle device in fluid communication with the fourth chamber of the aspiration means.

3. The volume homeostatic fluid—fluid exchanger according to claim 2, further comprising a first control valve disposed between the first chamber of the infusion means and the first needle device, the first control valve including a first port in fluid communication with the first needle device, a second port adapted to be in fluid communication with a medicine source, and a third port in fluid communication with the first chamber of the infusion means, wherein when the first control valve is in a first status, the first port is in fluid communication with the third port and when the first control valve is in a second status, the second port is in fluid communication with the third port.

4. The volume homeostatic fluid—fluid exchanger according to claim 2, further comprising a second control valve disposed between the fourth chamber of the aspiration means and the second needle device, the second control valve including a first port in fluid communication with the second needle device, a second port adapted to be in fluid communication with a drainage tube, and a third port in fluid communication with the fourth chamber of the aspiration means, wherein when the second control valve is in a first status, the first port is in fluid communication with the third port and when the first control valve is in a second status, the second port is in fluid communication with the third port.

5. The volume homeostatic fluid—fluid exchanger according to claim 1 wherein the first chamber of the infusion means and the fourth chamber of the aspiration means are identical in diameters thereof, and the second chamber of the infusion means and the third chamber of the aspiration means are identical in diameters thereof.

6. A volume homeostatic fluid—fluid exchanger comprising:
an infusion means including a first chamber and a second chamber defined therein, each of the first chamber and the second chamber having a first plungers slidably received therein, the first plungers being connected to move simultaneously;
an aspiration means including a third chamber and a fourth chamber, each of the third and the fourth chamber having a second plunger slidably received therein, the second plungers being connected to move simultaneously;
a connecting tube interconnected between the second chamber of the infusion means and the third chamber of the aspiration means, and a fluid being contained in the second chamber, the third chamber and the connecting tube;
a first control valve including a first port adapted to be in fluid communication with a first needle device, a second port adapted to be in fluid communication with a medicine source, and a third port in fluid communication with the first chamber of the infusion means, wherein when the first control valve is in a first status, the first port is in fluid communication with the third port and when the first control valve is in a second status, the second port is in fluid communication with the third port; and, a second control valve including a first port adapted to be in fluid communication with the second needle device, a second port adapted to be in fluid communication with a drainage tube, and a third port in fluid communication with the fourth chamber of the aspiration means, wherein when the second control valve is in a first status, the first port is in fluid communication with the third port and when the first control valve is in a second status, the second port is in fluid communication with the third port whereby when the first plunger of the first chamber of the infusion means moves in a direction, the second plunger of the fourth chamber of the aspiration means synchronously moves to a reverse direction of equal displacement due to the hydrodynamic synchronized action between the second chamber of the infusion means and the third chamber of the aspiration means.

7. The volume homeostatic fluid—fluid exchanger according to claim 6, further comprising a first needle device in fluid communication with the first port of the first control valve and a second needle device in fluid communication with the first port of the second control valve.

8. The volume homeostatic fluid—fluid exchanger according to claim 6, wherein the first chamber of the infusion means and the fourth chamber of the aspiration are identical in diameters thereof, and the second chamber of the infusion means and the third chamber of the aspiration are identical in diameters thereof.

\* \* \* \* \*